US010125397B2

(12) United States Patent
Brockman et al.

(10) Patent No.: US 10,125,397 B2
(45) Date of Patent: Nov. 13, 2018

(54) CANINE AUTOIMMUNE CONDITIONS AND DIAGNOSIS AND TREATMENT THEREOF

(71) Applicants: HILL'S PET NUTRITION, INC., Topeka, KS (US); THE TRANSLATIONAL GENOMICS RESEARCH INSTITUTE, Phoenix, AZ (US)

(72) Inventors: Jeffrey Brockman, Lawrence, KS (US); Matthew J. Huentelman, Phoenix, AZ (US)

(73) Assignees: HILL'S PET NUTRITION, INC., Topeka, KS (US); THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 38 days.

(21) Appl. No.: 15/039,333

(22) PCT Filed: Nov. 25, 2013

(86) PCT No.: PCT/US2013/071582
§ 371 (c)(1),
(2) Date: May 25, 2016

(87) PCT Pub. No.: WO2015/076832
PCT Pub. Date: May 28, 2015

(65) Prior Publication Data
US 2017/0166964 A1    Jun. 15, 2017

(51) Int. Cl.
| | | |
|---|---|---|
| *C07H 21/04* | (2006.01) | |
| *C12Q 1/68* | (2018.01) | |
| *C12Q 1/6883* | (2018.01) | |
| *A23K 50/40* | (2016.01) | |
| *A23K 20/10* | (2016.01) | |
| *A61K 36/82* | (2006.01) | |

(52) U.S. Cl.
CPC ............ *C12Q 1/6883* (2013.01); *A23K 20/10* (2016.05); *A23K 50/40* (2016.05); *A61K 36/82* (2013.01); *C12Q 2600/156* (2013.01)

(58) Field of Classification Search
None
See application file for complete search history.

(56) References Cited

U.S. PATENT DOCUMENTS

2016/0122822 A1* 5/2016 Martin .................. C12Q 1/6883
506/8

FOREIGN PATENT DOCUMENTS

JP    2009517071    4/2009

OTHER PUBLICATIONS

Serisier et al. (British J. or Nutrition, vol. 99, pp. 1208-1216, 2008). (Year: 2008).*
Nature's variety: Limited Ingredient Diet Lamb Meal formula https://web.archive.org/web/20110519224554/http://www.naturesvariety.com/instinct/dog/kibble/lidlamb, (Year: 2011).*
22 Green Tea Benefits for dogs (https://web.archive.org/web/20140702191845/http://store.ilovedogs.com/2013/04/22-ways-your-dog-can-benefit-from-green-tea-supplements/. Apr. 22, 2013 (Year: 2013).*
Chandra et al., "Catechin induced modulation in the activities of thyroid hormone synthesizing enzymes leading to hypothyroidism," Mol. Cell Biochem., 374: 37-48 (2013).
Chandra et al., "Effect of different doses of un-fractionated green and black tea extracts on thyroid physiology," Human and Experimental Toxicology, 30(8): 884-896 (2010).
Endurapet, "Your pet's struggling immune system can fight back~ with our meticulously formulated immune support supplement," Retrieved Oct. 23, 2017, from https://web.archive.org/web/20120618203308/http://www.endurapet.com/products/endurapet-immune-support.
International Search Report for International Application No. PCT/US2013/071582, prepared by the International Search Authority, dated Apr. 1, 2014, 7 pages.
Illumina, "CanineHD BeadChip," Retrieved Oct. 23, 2017, from https://www.illumina.com/documents/products/datasheets/datasheet_caninehd.pdf.
Kennedy et al., "Association of canine hypothyroidism with a common major histocompatability complex DLA class II allele," Tissue Antigens, 68: 82-86 (2006).
Kennedy et al., "Association of hypothyroid disease in Doberman Pinscher dogs with a rare major histocompatibility complex DLA class II haplotype," Tissue Antigens, 67: 53-56 (2006).
Nature's Variety, "Limited Ingredient Diet Lamb Meal Formula," Retrieved Oct. 23, 2017, from https://web.archive.org/web/20131114232220/http://www.naturesvariety.com/Instinct/dog/kibble/LIDlamb.
Royal Canin Veterinary Diet, "Nutrition for diabetic dogs," Retrieved Oct. 23, 2017, from http://www.royalcanin.co.uk/downloads/vetlibrary/information_for_owners_diabetic_dogs.PDF.
Salas et al., "Plant Polyphenol Intake Alters Gene Expression in Canine Leukocytes," Journal of Nutrigenetics and Nutrigenomics, 2(1): 43-52 (2009).
"Supplement Info; 22 Green Tea Benefits for Dogs," Retrieved Oct. 23, 2017, from http://store.ilovedogs.com/2013/04/22-ways-your-dog-can-benefit-from-green-tea-supplements.
JP2009517071, Mars, Inc., "MHC Alleles," Apr. 30, 2009, English language machine translation of abstract, Espacenet, date obtained: Feb. 20, 2018, 1 page, <URL: https://worldwide.espacenet.com/publicationDetails/biblio?CC=JP&NR=2009517071A&KC=A&FT=D&ND=3&date=20090430&DB=&locale=en_EP>.

* cited by examiner

*Primary Examiner* — Jeanine A Goldberg
(74) *Attorney, Agent, or Firm* — Hoxie & Associates LLC

(57) ABSTRACT

The disclosure includes methods of identifying a dog at risk of developing a an autoimmune disease or condition, for example a hypothyroid disease or condition, comprising testing whether the dog exhibits one or more selected single nucleotide polymorphisms (SNPs), together with diagnostic kits for carrying out such methods, methods of treatment or prophylaxis of such autoimmune disease or condition, e.g., comprising administering an effective amount of tea extract to a dog in need thereof, and a canine diet or supplement comprising tea extract, useful for treatment of prophylaxis of such autoimmune disease or condition, or for maintenance of thyroid health in a dog.

6 Claims, No Drawings

CANINE AUTOIMMUNE CONDITIONS AND DIAGNOSIS AND TREATMENT THEREOF

CROSS-REFERENCE TO RELATED APPLICATIONS

This application is a National Stage Entry of International Application No. PCT/US2013/071582, filed on Nov. 25, 2013, the contents of which are hereby incorporated by reference.

BACKGROUND

Canine hypothyroidism is the most common endocrine problem in dogs. It is characterized by insufficient levels of thyroid hormones (T3/T4). Metabolic consequences include weight gain, lethargy, intolerance to cold, a slow heart rate, absence of heat cycles, and lethargy. The dogs typically exhibit hair loss and brittle coat, and skin which is dry, thick, puffy, and darkly pigmented. Some dogs develop secondary seborrhea. Estimates of incidence range from 1 in 156 to 1 in 500 animals. The onset of disease is typically in middle age (4-6 years). Current treatment is typically with thyroid hormone supplementation, generally with synthetic L-thyroxine (L-T4). The prognosis for dogs that respond to therapy is good; however this is a progressive disease, and the dogs should be monitored regularly and the medication dose adjusted as needed. There are two histological classifications of primary hypothyroidism. The first, lymphocytic thyroiditis, is characterized by lymphocytic infiltration of the thyroid tissue, and the second, idiopathic atrophy, is thought to be the end stage to lymphocytic thyroiditis where the thyroid tissue has been mostly destroyed. Canine hypothyroidism is believed to be an autoimmune condition, and antibodies against thyroid hormone and thyroglobulin are often found in the serum of affected dogs. There is also a breed predisposition for hypothyroidism, indicating that there is some heritable component to the disease and that genetic association studies may give some insight into the disease.

Accurate diagnosis of hypothyroidism presents challenges. While a normal level of free T4 generally indicates that the dog does not have hypothyroidism, a low-normal or below-normal level in a single test does not necessarily mean the dog is hypothyroid. A more accurate diagnosis can be obtained by a full thyroid panel test that evaluates both free and total T3 and T4 as well as auto-antibodies against the thyroid hormones. Assays for thyroglobulin autoantibodies may also be used, but these autoantibodies are present at detectable levels only in about 50 percent of dogs with autoimmune thyroiditis. Although certain organizations maintain a hypothyroid registry to help identify whether dogs are suitable for breeding, no specific genetic markers for canine hypothyroidism have been disclosed. Diagnosis often comes after the dogs have already been bred. Hypothyroidism is a progressive autoimmune disease so there is an advantage to diagnosing and treating an animal early in the onset of disease in addition to identifying the animal as a potential carrier for the condition. There is a need for improved methods of identifying and treating dogs at elevated risk of this disease.

Other autoimmune diseases or conditions of dogs include lymphocytic thyroiditis and idiopathic atrophy of the thyroid, rheumatoid arthritis, systemic lupus erythematosus (SLE), discoed lupus, auto-immune hemolytic anemia (AIHA), or pemphigus. As in the case of hypothyroid disease, there is a need for improved methods of identifying and treating dogs at elevated risk of such diseases, particularly as early treatment, before there is irreversible tissue or organ damage, is critically important.

BRIEF SUMMARY

In one embodiment, the invention provides a method of identifying a dog at risk of developing a an autoimmune disease or condition, for example a hypothyroid disease or condition, for example lymphocytic thyroiditis and idiopathic atrophy of the thyroid, comprising testing whether the dog exhibits one or more single nucleotide polymorphisms (SNPs) selected from the SNPs listed on Table 1, below, or SNPs located at or near the locus of the TNIP3 gene on dog chromosome 19. In another embodiments, the invention provides a diagnostic kit for carrying out such a method. In another embodiment, the invention provides methods of treatment or prophylaxis of an autoimmune disease or condition comprising administering an effective amount of tea extract to a dog in need thereof. In another embodiment, the invention provides a canine diet or supplement comprising tea extract.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In the context of the invention, the term "treating" or "treatment", as used herein, means reversing, alleviating, mitigating or inhibiting the progress of the disorder or condition to which such term applies, or one or more symptoms of such disorder or condition. As used herein and in the appended claims, the singular forms "a", "an", and "the" include plural reference unless the context clearly dictates otherwise.

In one embodiment, the invention provides a method (Method 1) of identifying a dog at risk of developing an autoimmune disease or condition, comprising testing whether the dog exhibits one or more single nucleotide polymorphisms (SNPs) selected from the SNPs listed on Table 1, below and SNPs at or near the locus of the MIN gene on dog chromosome 19, e.g., 1.1. Method 1 wherein the autoimmune disease is selected from hypothyroid disease, rheumatoid arthritis, systemic lupus erythematosus (SLE), discoid lupus, auto-immune hemolytic anemia (AIHA), type 1 diabetes, or pemphigus.

1.2. Method 1 or 1.1 wherein the autoimmune disease or condition is a hypothyroid disease or condition, for example lymphocytic thyroiditis and idiopathic atrophy of the thyroid.

1.3. Any preceding method wherein the presence of one or more SNPs is measured by a method selected from selected from (i) hybridization methods utilizing sequence specific oligonucleotide probes (e.g., dynamic allele-specific hybridization, molecular beacons, or SNP microarrays), (ii) enzyme-based techniques such as restriction fragment length polymorphism (RFLP), polymerase chain reaction methods (e.g., tetra-primer ARMS-PCR with specific primers which can allow detection of the SNPs), flap endonuclease which allows detection of single nucleotide mismatches, primer extension techniques (e.g., hybridization of a probe to the bases immediately upstream of the SNP nucleotide followed by a 'mini-sequencing' reaction, in which DNA polymerase extends the hybridized primer by adding a base that is complementary to the SNP nucleotide), 5'-nucleases using forward and reverse PCR primers that will amplify a region that includes the SNP, and oligonucleotide ligation assays, and (iii) post-amplification methods based on physical properties of DNA, such as single strand conformation polymorphism, temperature gradient gel electrophoresis, denaturing high performance liquid chromatography, high-resolution melting of the entire amplicon, use of DNA mismatch-binding proteins, and commercial systems such as SNPlex (Applied Biosystems).

1.4. Any preceding method wherein the one or more SNPs are identified using a SNP microarray, e.g., an Illumina CanineHD BeadChip (http://res.illumina.com/documents/products/datasheets/datasheet_caninehd.pdf).

1.5. Any of the foregoing methods wherein the SNPs include one or more SNPs at or near the locus of the TNIP3 gene on Chromosome 19.

1.6. Any of the foregoing methods wherein the SNPs are selected from one or more of the SNPs identified on Table 1.

1.7. Any of the foregoing methods wherein the SNPs include one or more SNPs selected from BICF2P67, TIGRP2P2, BICF2S23, and BICF2P89.

In another embodiment, the invention provides a diagnostic kit (Kit 1) for identifying a dog at risk of developing an autoimmune disease or condition, e.g., hypothyroid disease or condition, for example lymphocytic thyroiditis and idiopathic atrophy of the thyroid, comprising a sequence specific oligonucleotide probe which recognizes one or more single nucleotide polymorphisms (SNPs) selected from the SNPs listed on Table 1 and SNPs at or near the locus of the TNIP3 gene on Chromosome 19, together with instructions for use.

1.1. Kit 1 wherein the autoimmune disease is selected from hypothyroid disease, rheumatoid arthritis, systemic lupus erythematosus (SLE), discoid lupus, auto-immune hemolytic anemia (AIHA), type 1 diabetes, or pemphigus.

1.2. Kit 1 or 1.1 wherein the autoimmune disease or condition is a hypothyroid disease or condition, for example lymphocytic thyroiditis and idiopathic atrophy of the thyroid.

1.3. Any preceding kit wherein the SNPs include one or more SNPs at or near the locus of the TNIP3 gene on Chromosome 19.

1.4. Any of the foregoing methods wherein the SNPs include SNPs selected from one or more of the SNPs identified on Table 1.

1.5. Any of the foregoing methods wherein the SNPs include one or more SNPs selected from BICF2P67, TIGRP2P2, BICF2S23, and BICF2P89.

In another embodiment, the invention provides a method of treatment or prophylaxis of an autoimmune disease or condition, e.g., hypothyroid disease or condition, for example lymphocytic thyroiditis and idiopathic atrophy of the thyroid, in a dog, comprising identifying a dog at risk of developing a hypothyroid disease or condition, by any of Method 1, et seq., and administering to a dog so identified an effective amount of an anti-inflammatory medication or natural product/functional ingredient that regulates the transcription factor NF-kappaB which is responsible for shaping the immune T cell repertoire, and whose dysfunction can lead to autoimmune disease.

In another embodiment, the invention provides a method (Method 2) of treatment or prophylaxis of an autoimmune disease or condition in a dog, e.g., an autoimmune condition mediated by TNFα and/or interleukin 6 (IL-6), e.g., selected from hypothyroid disease, rheumatoid arthritis, systemic lupus erythematosus (SLE), discoid lupus, auto-immune hemolytic anemia (AIHA), type 1 diabetes, or pemphigus, comprising administering an effective amount of tea extract to a dog in need thereof, e.g.

2.1. Method 2 wherein the dog in need of such treatment is identified as having, or being at elevated risk of developing, an autoimmune disease or condition using any of Methods 1, et seq.

2.2. Method 2 or 2.1 wherein the autoimmune disease or condition is hypothyroid disease, for example lymphocytic thyroiditis and idiopathic atrophy of the thyroid 2.3. Any foregoing method wherein the tea extract is provided in an amount sufficient to provide a peak plasma concentration of 1-2 µg/ml.

2.4. Any preceding method wherein the tea extract is administered in the form of a diet which is palatable and nutritionally complete for a dog, which diet comprises tea extract.

2.5. Any preceding method wherein the tea extract is administered in the form of a diet according to any of Diet 1, et seq.

2.6. Any preceding method wherein the tea extract is decaffeinated.

In another embodiment, the invention provides a canine diet (Diet 1), e.g., a diet which is palatable and nutritionally complete for a dog, e.g., a dog having, or at elevated risk of developing, an autoimmune condition in a dog, e.g., an autoimmune condition mediated by TNFα and/or interleukin 6 (IL-6), e.g., selected from hypothyroid disease, rheumatoid arthritis, systemic lupus erythematosus (SLE), discoid lupus, auto-immune hemolytic anemia (AIHA), type 1 diabetes, or pemphigus, for example a diet for maintaining thyroid health in a dog, wherein the diet comprises an effective amount of tea extract, e.g., 1.1. Diet 1 wherein the diet is palatable and nutritionally complete for a dog.

1.2. Diet 1 or 1.1 wherein the amount of tea extract is 0.1-5 mg/kg, e.g. 0.1-1 mg/kg.

1.3. Any preceding diet wherein the tea extract is decaffeinated.

In a further embodiment, the invention provides the use of a tea extract in the manufacture of a diet for treatment or prophylaxis of an autoimmune disease or condition in a dog, e.g. any of Diet 1, et seq.

In a further embodiment the invention provides tea extract for use in the treatment or prophylaxis of an autoimmune disease or condition in a dog, e.g., in accordance with any of Methods 2, et seq.

In a further embodiment, the invention provides a method (Method 3) for maintaining thyroid health in a dog, comprising administering to the dog an effective amount of tea extract, e.g., 3.1. Method 3 wherein the dog has or is at elevated risk of hypothyroid disease or condition, for example lymphocytic thyroiditis and idiopathic atrophy of the thyroid.

3.2. Method 3 or 3.1 wherein the dog is identified as having, or being at elevated risk of developing, an autoimmune disease or condition using any of Methods 1, et seq.

EXAMPLES

Example 1

We performed a genome-wide association study (GWAS) on 50 dogs clinically diagnosed with hypothyroidism and 566 case controls. The dogs were genotyped with Illumina's Infinium HD CanineHD bead chip, representing over 170,000 single nucleotide polymorphisms evenly spaced across the dog genome. We identified particular loci containing one or more SNPs with a highly significant association to the hypothyroid phenotype (p on the order of $10^{-7}$ or $10^{-8}$), as depicted on Table 1:

TABLE 1

| CHR | SNP | BP | A1 | TEST | NMISS | OR | STAT | P | GENE |
|---|---|---|---|---|---|---|---|---|---|
| 1 | BICF2S2291826 | 109082442 | A | ADD | 598 | 3.101 | 5.178 | 2.25E−07 | KLK14 |
| 5 | BICF2P644940 | 32018566 | G | ADD | 598 | 2.91 | 5.143 | 2.71E−07 | mmp3 |
| 5 | BICF2S23620647 | 48768926 | G | ADD | 597 | 2.934 | 4.919 | 8.68E−07 | |
| 5 | BICF2P1010252 | 48773672 | A | ADD | 598 | 2.939 | 4.928 | 8.29E−07 | UBE2U |
| 6 | BICF2S2299083 | 63965090 | C | ADD | 566 | 3.655 | 5.343 | 9.14E−08 | LMO4 |
| 7 | BICF2P325158 | 78980520 | A | ADD | 598 | 2.895 | 5.046 | 4.52E−07 | VAPA |
| 13 | BICF2G630619848 | 32292493 | G | ADD | 598 | 3.004 | 4.976 | 6.51E−07 | TG |
| 13 | BICF2G630664672 | 32998675 | A | ADD | 598 | 3.18 | 4.99 | 6.03E−07 | TG |
| 14 | BICF2S2309682 | 26627034 | G | ADD | 598 | 4.637 | 5.156 | 2.53E−07 | |
| 19 | BICF2P676019 | 21913501 | A | ADD | 598 | 3.748 | 5.364 | 8.12E−08 | TNIP3 |
| 19 | TIGRP2P259868__rs8826879 | 21963920 | A | ADD | 598 | 3.18 | 5.167 | 2.37E−07 | TNIP3 |
| 19 | BICF2S23412424 | 21970802 | T | ADD | 598 | 3.18 | 5.167 | 2.37E−07 | TNIP3 |
| 19 | BICF2P891737 | 21978107 | C | ADD | 595 | 3.151 | 5.121 | 3.03E−07 | TNIP3 |
| 19 | BICF2G63043222 | 23950538 | A | ADD | 596 | 3.255 | 5.003 | 5.64E−07 | PLEKHB2 |
| 19 | BICF2G63041470 | 24819071 | G | ADD | 597 | 3.741 | 5.032 | 4.85E−07 | Pqbp1 |
| 19 | BICF2P1049515 | 25239827 | A | ADD | 598 | 3.783 | 5.295 | 1.19E−07 | TADA1 |
| 19 | BICF2G63044580 | 25251446 | G | ADD | 598 | 3.783 | 5.295 | 1.19E−07 | |
| 19 | BICF2G63044702 | 25925990 | G | ADD | 598 | 3.126 | 5.163 | 2.43E−07 | |
| 19 | BICF2S23139628 | 32148097 | G | ADD | 598 | 3.286 | 4.895 | 9.81E−07 | CLASP1 |
| 20 | BICF2P777635 | 51403698 | G | ADD | 598 | 3.108 | 5.433 | 5.56E−08 | ASF1B |
| 20 | BICF2P1281945 | 56168011 | G | ADD | 598 | 2.852 | 5.097 | 3.45E−07 | ACTL9 |
| 31 | BICF2P782092 | 7378002 | G | ADD | 598 | 5.827 | 5.412 | 6.22E−08 | SMAD2 |
| 31 | BICF2G630734810 | 21004766 | G | ADD | 598 | 2.806 | 4.906 | 9.28E−07 | CLNS1A |
| 31 | BICF2G630741339 | 34096864 | A | ADD | 598 | 4.827 | 4.988 | 6.09E−07 | SIM2 |
| 31 | BICF2P1171495 | 40784356 | A | ADD | 593 | 3.904 | 5.043 | 4.58E−07 | SUMO3 |
| 31 | BICF2P989266 | 40802884 | A | ADD | 598 | 3.774 | 4.957 | 7.14E−07 | UBE2G2 |
| 38 | BICF2S22955325 | 22793576 | C | ADD | 579 | 6.511 | 5.068 | 4.03E−07 | RGS4 |

3.3. Any preceding method wherein the tea extract is provided in an amount sufficient to provide a peak plasma concentration of 1-2 μg/ml.

3.4. Any preceding method wherein the tea extract is administered in the form of a diet which is palatable and nutritionally complete for a dog, which diet comprises tea extract.

3.5. Any preceding method wherein the tea extract is administered in the form of a diet according to any of Diet 1, et seq.

3.6. Any preceding method wherein the tea extract is decaffeinated.

3.7. Any preceding method wherein the tea extract is administered in the form of a diet which is palatable and nutritionally complete for a dog, which diet comprises tea extract, wherein the diet is administered over a period of at least a month, e.g., at least six months, e.g., at least a year.

In another embodiment, the invention provides the use of a tea extract in the manufacture of a diet for maintaining thyroid health in a dog, e.g. wherein the diet is any of Diet 1, et seq.

In a further embodiment the invention provides tea extract for use in maintaining thyroid health in a dog, e.g., in accordance with any of Methods 3, et seq.

Genotype analysis for one or more of the above-listed significant SNP genetic markers provides a useful method for identifying susceptibility to the development of hypothyroidism in dogs.

Of particular interest was a locus with four significant markers in and around the TNIP3 gene located on chromosome 19. The TNIP3 gene encodes for a protein that binds to A20, a protein that regulates the signal transduction pathways leading to the activation of the transcription factor Nuclear Factor kappa B (NF-κB). Over-expression of TNIP3 can down regulate NF-κB activity independent of its interaction with A20 indicating that it may regulate immune function both in an A20 dependent and independent manner. TNIP3 has not been associated with hypothyroidism in dogs or humans or any other autoimmune disorder. However, A20 has been associated with human autoimmune disorders such as systemic lupus erythematosus, rheumatoid arthritis, celiac disease/ulcerative colitis, and psoriasis. Also a paralog to TNIP3, TNIPI, which is also known to be able to down regulate NF-κB activity, is associated with human autoimmune disorders such as psoriatic arthritis, rheumatoid arthritis, and systemic lupus erythematosus. NF-κB is known to be involved in the differentiation and development of cells that regulate autoimmunity such as Th 17 and T reg cells.

This supports the idea that disruption of the normal function of TNIP3 could lead to altered NF-κB function that contributes to the development of autoimmunity and the development of hypothyroidism in dogs. Furthermore, it is possible that food additives or supplements that can compensate for the defective TNIP3 genes by down regulating NF-κB activity, may slow the development and/or progression of autoimmunity that results in progression of canine hypothyroidism.

One of the key genes induced by NF-κB is Tumor Necrosis Factor alpha (TNFα). TNFa in turn activates NF-κB in a feed forward mechanism which when unchecked can contribute to inflammation and autoimmune dysfunction. In fact, elevated levels of TNFα are found in the serum of humans with hypothyroidism. Furthermore, when hypothyroidism is corrected for by treatment with synthetic thyroid hormone, TNFα levels do not return to baseline indicating that the autoimmune condition with elevated TNFα levels is an underlying cause of the condition and not merely an effect of reduced thyroid hormone. In fact TNFα may be a good biomarker for effective in vivo and in vitro treatment of hypothyroidism in dogs.

When the canine monocyte cell line DH-82 is treated with LPS, NF-κB is rapidly activated and TNFa levels induced 50-60 fold at 2 hours post treatment. LPS induces TNIP3 gene expression which peaks at 4 hours post treatment and corresponds to a reduction in TNFα expression. Both TNFα and TNIP3 levels decrease by 8 hours post treatment indicating that NE-κB activation has been attenuated.

As an example of how a nutritional ingredient/supplement can inhibit the induction of TNFα, we treated DH-82 cells with increasing amounts of a cold water black tea extract. The tea extract inhibited the LPS induced expression of both TNFα and the pro-inflammatory cytokine interleukin 6 (IL-6) in a dose-dependent manner, with an $EC_{50}$ of approximately 2 μg/ml.

What is claimed is:

1. A method for maintaining thyroid health in a dog, comprising
   a) obtaining a biological sample from the dog,
   b) assaying the biological sample from the dog for one or more single nucleotide polymorphisms (SNPs) wherein the one or more SNPs comprises BICF2P676019,
   c) detecting an A allele at BICF2P676019 in the biological sample from the dog, and
   d) administering an effective amount of tea extract to the dog with an A allele at BICF2P676019 to maintain the thyroid health of the dog.

2. The method of claim 1 wherein the tea extract is administered in the form of a diet which is palatable and nutritionally complete for a dog and which diet comprises tea extract.

3. The method of claim 2, wherein the amount of tea extract in the diet is 0.1-5 mg/kg.

4. The method of claim 1, further comprising assaying for one or more SNPs selected from the group consisting of an "A" at TIGRP2P259868 rs8826879, a "T" at BICF2S23412424 and a "C" at BICF2P891737.

5. The method of claim 1, wherein the tea extract is decaffeinated.

6. The method of claim 1, further comprising assaying for one or more SNPs selected from the group consisting of an "A" at BICF2S2291826, a "G" at BICF2P644940, a "G" at BICF2S23620647, an "A" at BICF2P1010252, a "C" at BICF2S2299083, an "A" at BICF2P325158, a "G" at BICF2G630619848, an "A" at BICF2G630664672, a "G" at BICF2S2309682, an "A" at TIGRP2P259868_rs8826879, a "T" at BICF2S23412424, a "C" at BICF2P891737, an "A" at BICF2G63043222, a "G" at BICF2G63044170, an "A" at BICF2P1049515, a "G" at BICF2G63044580, a "G" at BICF2G63044702, a "G" at BICF2S23139628, a "G" at BICF2P777635, a "G" at BICF2P1281945, a "G" at BICF2P782092, a "G" at BICF2G630734810, an "A" at BICF2G630741339, an "A" at BICF2P1171495, an "A" at BICF2P989266, and a "C" at BICF2S22955325.

* * * * *